United States Patent [19]

Van der Salm

[11] Patent Number: Plant 6,285

[45] Date of Patent: Sep. 13, 1988

[54] LILY PLANT: CORSICA

[76] Inventor: Gerardus C. Van der Salm, Rte. 1, Box 422, Woodland, Wash. 98674

[21] Appl. No.: 902,461

[22] Filed: Aug. 29, 1986

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Klarquist, Sparkman, Campbell, Leigh & Whinston

[57] ABSTRACT

A new variety of hybrid lily plant bearing large clusters of flowers of excellent form and long persistence, both on the plant and as cut-flowers. The flowers of the new plant are particularly characterized by their cream white/clear pink bicolor pattern and by their inconspicuous spotting. This combination is completely new in the upright Asiatic divisions of lilies suited to forcing and to mass commercial cultivation. The plant is highly resistant to disease and shows high tolerance of virus. It is an excellent garden plant. The bulbs may be precooled and forced for cut-flower production. The new lily plant is vigorous and is a good grower and propagator.

1 Drawing Sheet

BACKGROUND AND SUMMARY OF THE INVENTION

This invention relates to a new and distinct variety of lily classified botannically as a lilium hybrid and commercially as an upright Asiatic hybrid. I have selected the name "Corsica" as the varietal name for my plant.

My new variety of lily plant originated as a seedling selected from a group of seedlings at Julianadorp, The Netherlands. The seedlings were planted as a result of breeding efforts carried on by me since 1976. The breeding efforts had as their objective the production of spotless or inconspicuously spotted upright Asiatic lilies in shades of pink and rose, well suited to forcing for cut-flower production out of season, heretofore unknown in the lily breeding art.

I achieved the desired objective by extensive interpollinations among many hybrid lily cultivars.

The flowers of my new lily are characterized by an upright orientation and a distinctive cream white/clear pink two-toned color pattern. More specifically, the tepals of the flowers of my new lily plant have cream white throats suffusing to rich pink tips, accented by clear pink nectaries and a deeper pink "sliver" extending from them, and accentuated by inconspicuous spotting. This color pattern is unique among Asiatic hybrid lilies and in particular among those suited to forcing and to mass commercial cultivation.

In addition, my new lily plant possesses to a high degree desirable characteristics of hybrid vigor, great hardiness, and disease resistance, including a high tolerance of virus. It possesses all of the desired characteristics of excellence of form, color and habit. Its excellently formed flowers, of large size, are produced on a single stalk. The new lily plant is vigorous, a good grower, and a rapid propagator, as observed at Julianadorp, The Netherlands, and at Woodland, Wash.

My new lily plant has versatility both as a garden plant and as a cut flower producer. It is well suited to forcing out of season when the bulbs are dug at the appropriate time and properly precooled. For example, October-dug bulbs, properly precooled and potted in January, will flower under glass in Western Oregon, with no supplementary lighting and at moderate greenhouse temperatures, in an average of seventy to seventy-five days.

My new variety of Asiatic hybrid lily most nearly resembles the variety "Zephyr," but my new variety has a distinctive cream white/deeper color pink bicolor pattern, rather than the single and lighter pink shade of "Zephyr." Its flowers have fewer and less conspicuous spots, and they also carry a distinctive deeper-toned "sliver" of color extending 2 to 4 cm from the nectary furrows. "Corsica" has rounder-tipped and more cup-shaped tepals than "Zephyr." It is also a more reliable variety for forcing out of season, with stronger stems; and it has darker stems and leaves, deeper pink bud color and a more compact inflorence.

My new variety of lily plant has been asexually reproduced by me and under my direction at Julianadorp, The Netherlands and at Woodland, Wash. Successive generations produced by bulb scale propagation and by natural propagation from bulblets have demonstrated that the novel and distinctive characteristics of my new variety are fixed and hold true under asexual propagation from generation to generation.

DESCRIPTION OF THE DRAWING

The new variety of lily plant is illustrated in the accompanying photographic drawing, which shows the open bloom in full color and illustrates the flower form, the tepal arrangement, the connection of the flower to the stem, and in particular the novel and distinctively bicolored cream white/clear pink inconspicuously spotted flowers.

DETAILED DESCRIPTION OF MY NEW VARIETY

The following is a detailed description of my new variety of Asiatic hybrid lily, with nomenclature according to the *International Lily Register* (Royal Horticultural Society of London, Second Edition, 1969), and with color designations according to the Colour Chart of The Royal Horticultural Society, published by the Society in 1966.

THE PLANT

Origin: Seedling.

Seed parent: Unnamed seedling.
Pollen parent: Unnamed seedling.
Commercial classification: Hybrid Lilium clone.
Horticultural classification: Division I-A, upright Asiatic hybrid lily, according to the Horticultural Classification of Lilies, Royal Horticultural Society of London.
Form: Single stem, erect and stately.
Height: 70–100 cm from bulbs 15 to 18 cm in circumference, provided their light levels are adequate; low light levels may cause "stretching".
Growth: Vigorous and upright.
Foliage quantity: Abundant.
Size of leaf: 8 to 12 cm long×5 to 12 mm wide.
Shape of leaf: Lanceolate (pointed).
Texture: Leathery and glossy.
Color: Dark green, lighter on lower side.
Bulb size: Any size, ranging to 25 cm circumference commercially.
Bulb color: White.

THE BUD

Form: Obtuse, ovoid and long.
Size: 8 to 9 cm long and 5 cm in circumference just prior to opening.
Opening: Bud opens slowly, in response to morning light; this takes about one hour.
Color: RHS CC red-purple 62 B-D, with a 2–3 mm wide flush of RHS CC 64 C at the apex of each tepal.
Peduncle: Averages 4 to 6 cm, but it may elongate if light levels are too low or if bulbs have been improperly stored prior to forcing. Color is dark green with light plum overlay.

THE FLOWER

Blooming habit: Annually in midseason; flowers once and profusely.
Size: Flowers are large-sized for Asiatic hybrids. They average 14 to 17 cm in diameter; the outer tepals are 2 to 2.5 cm wide, and the inner tepals are 3 cm wide.
Borne: In a single racemic inflorescence producing 7 to 12 buds (from a bulb 18 cm in circumference)
Shape: First open in cup shape, which flattens as tepals recurve by their second day.
Tepalage: Typical of genus Lilium, with 6 imbricated tepals.
Tepal color: Flowers are distinguished by their cream white/clear pink bicolored pattern. The center of the tepals is palest cream to white, extending 2 cm into the tepal, where it is then overlaid with a clear pink pigmentation that deepens as it extends to the tips of the tepals. The pink color is RHS CC red-purple 62 A-B nearer the base of the tepal, deepening to RHS CC 63 B-C at the apex. The pink color is affected by temperature and light levels; it decreases with very high temperatures and with low light levels. The nectary furrows are lightly pubescent and are soft pink, RHS CC 62 B-C; and a band of deeper-toned pink, RHS CC 63 C, extends 2 to 4 cm along the center of the tepal from the nectary furrow.

Tepal spotting: Spotting is inconspicuous; there are a very few tiny deep magenta spots at the base of each tepal, parallel to the upper end of the nectary furrows.
Tepal longevity: Tepals stay on stems about three weeks.
Pedicel length: Average 6 to 8 cm long.
Pedicel color: Deep green with light plum overlay.
Pedicel form: Sturdy and ascending up to 45 degrees from the horizontal. Occasional secondary buds.
Color changes: Flowers become slightly lighter and a more lavender-toned pink, approaching RHS CC 69 A with RHS CC 68 B-C tips and "sliver" extending from the nectary furrow, as they age. Low light levels and extreme heat may cause the pink pigmentation to decrease.
Appearance: Flower is shiny.
Disease resistance: The flower and plant are resistant to disease; in particular, they are resistant to Fusarium bulb rot and Botrutis blight.
Fragrance: None.
Lasting quality: The flower is long lasting, both on the plant and as a cut-flower.

THE REPRODUCTIVE ORGANS

Stamens and anthers: Arrangement typical of genus Lilium. Six stamens with soft pink RHS CC 62 D filaments 5 cm long.
Pollen and anthers (dehisced): RHS CC greyed red 179 A.
Pistil: One in number, 5 cm long.
Stigma: Soft cream to very light pink, medium in size.
Characteristics of ovary: Characteristic of genus Lilium.

THE FRUIT

Fertility: The fruit is fertile.
Shape: Ovoid.
Color at maturity: Soft brown, sometimes overlaid with soft plum.

I claim:

1. A new and distinctive variety of Asiatic hybrid lily plant substantially as herein shown and described and characterized in particular by the color pattern of its flowers which have tepals with cream white throats suffusing to rich pink tips, accented by clear pink nectaries and a deeper pink "sliver" extending from them, and accentuated by inconspicuous spotting.

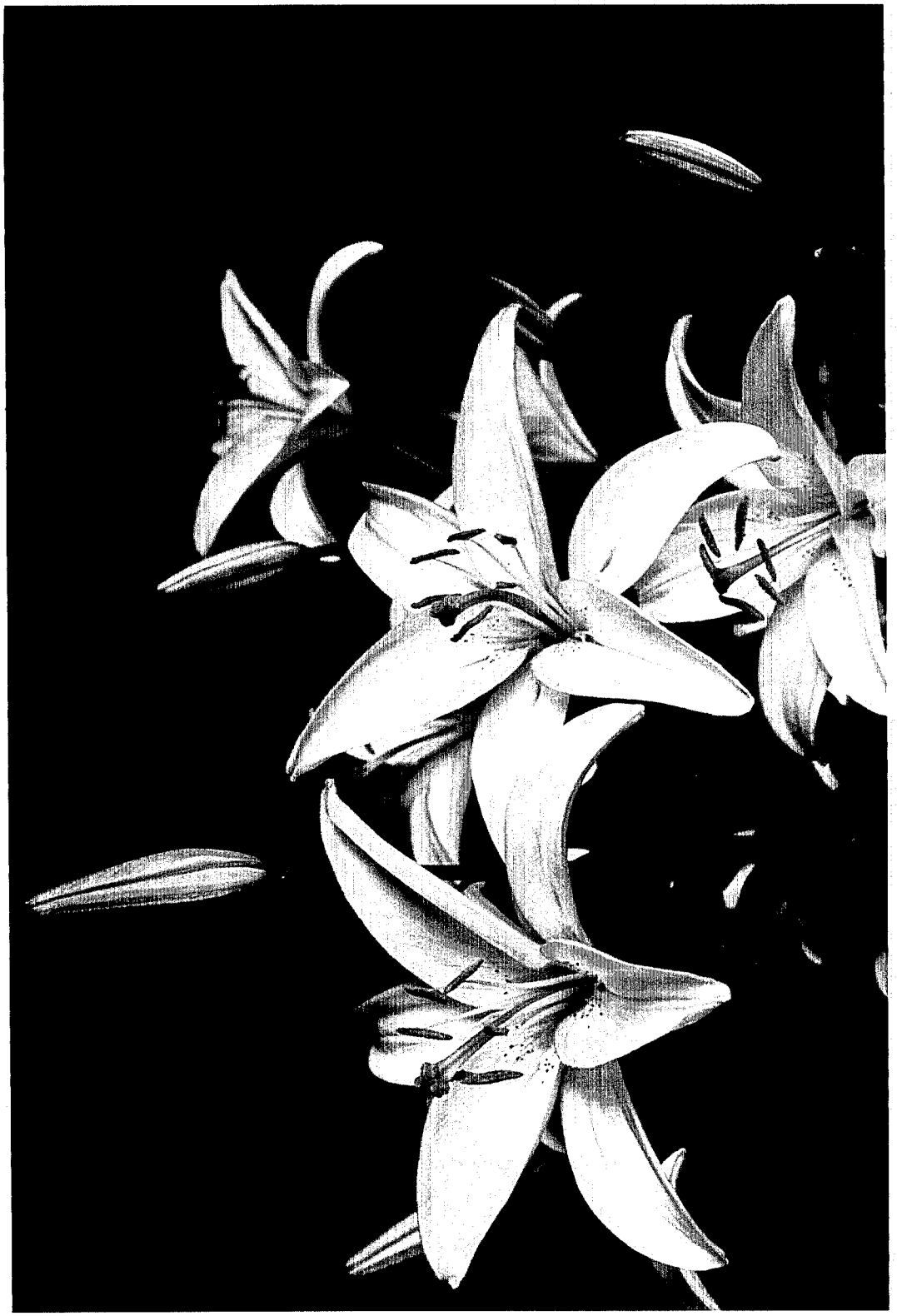

* * * * *